United States Patent
Shah et al.

(10) Patent No.: US 9,048,012 B2
(45) Date of Patent: Jun. 2, 2015

(54) METHOD OF FABRICATING HIGH-DENSITY HERMETIC ELECTRICAL FEEDTHROUGHS

(75) Inventors: Kedar G. Shah, San Francisco, CA (US); Satinderpall S. Pannu, Pleasanton, CA (US); Terri L. Delima, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 0 days.

(21) Appl. No.: 14/009,332

(22) PCT Filed: Apr. 18, 2012

(86) PCT No.: PCT/US2012/034111
§ 371 (c)(1),
(2), (4) Date: Oct. 1, 2013

(87) PCT Pub. No.: WO2012/145419
PCT Pub. Date: Oct. 26, 2012

(65) Prior Publication Data
US 2014/0020951 A1    Jan. 23, 2014

Related U.S. Application Data

(60) Provisional application No. 61/476,615, filed on Apr. 18, 2011.

(51) Int. Cl.
*H02G 3/04* (2006.01)
*H01B 13/06* (2006.01)
*A61N 1/375* (2006.01)
*H05K 3/44* (2006.01)

(52) U.S. Cl.
CPC .............. *H01B 13/06* (2013.01); *A61N 1/3754* (2013.01); *H05K 3/445* (2013.01); *H02G 3/04* (2013.01)

(58) Field of Classification Search
CPC .......... H01B 13/06; H01B 13/00; H02G 3/04; H02G 3/00; H02G 3/02; H05K 3/445; H05K 3/44; A61N 1/3764
USPC ................ 174/667, 650, 152 GM, 520, 50.5, 174/50.61; 361/602, 606.1, 607, 306.2, 361/328, 329, 306.1, 307, 302; 607/36, 5; 264/104, 400, 485; 216/19; 29/592, 29/592.1
See application file for complete search history.

(56) References Cited

U.S. PATENT DOCUMENTS

| | | | | |
|---|---|---|---|---|
| 5,245,999 A * | 9/1993 | Dahlberg et al. | ............ | 607/9 |
| 5,959,829 A * | 9/1999 | Stevenson et al. | ............ | 361/302 |
| 6,424,234 B1 * | 7/2002 | Stevenson | ............ | 361/302 |
| 7,310,216 B2 * | 12/2007 | Stevenson et al. | ............ | 361/302 |
| 7,391,601 B1 * | 6/2008 | Imani | ............ | 361/302 |
| 2005/0040513 A1 * | 2/2005 | Salmon | ............ | 257/698 |

* cited by examiner

*Primary Examiner* — Angel R Estrada
(74) *Attorney, Agent, or Firm* — James S. Tak

(57) ABSTRACT

A method of fabricating electrical feedthroughs selectively removes substrate material from a first side of an electrically conductive substrate (e.g. a bio-compatible metal) to form an array of electrically conductive posts in a substrate cavity. An electrically insulating material (e.g. a bio-compatible sealing glass) is then flowed to fill the substrate cavity and surround each post, and solidified. The solidified insulating material is then exposed from an opposite second side of the substrate so that each post is electrically isolated from each other as well as the bulk substrate. In this manner a hermetic electrically conductive feedthrough construction is formed having an array of electrical feedthroughs extending between the first and second sides of the substrate from which it was formed.

17 Claims, 8 Drawing Sheets

US 9,048,012 B2

METHOD OF FABRICATING HIGH-DENSITY HERMETIC ELECTRICAL FEEDTHROUGHS

CROSS-REFERENCE TO RELATED APPLICATIONS

This patent document claims the benefits and priorities of U.S. Provisional Application No. 61/476,615, filed on Apr. 18, 2011, hereby incorporated by reference.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

This patent document relates to methods of fabricating hermetic electrical feedthroughs, and in particular to a method of fabricating high-density hermetic electrical feedthroughs from an electrically conductive substrate material.

BACKGROUND

Electrically-active implantable bio-medical devices (such as for example pacemakers, cochlear implants, and neural prosthetics) are increasing in popularity due to the potential of continuous monitoring, instantaneous and directed delivery of treatments, reduction of treatment costs, and unique treatment options. However, because many of the component materials used in such devices are not bio-compatible, that is, they are toxic to the body and can induce undesirable biological reactions, it is critical to hermetically seal the non-bio-compatible components (e.g. CMOS, passive components, batteries) in a bio compatible material, so that the body does not have a cyto-toxic response. Hermetic sealing also helps protects electrical components from damage due to moisture and the corrosive environment in the body. FIG. 1 shows a schematic illustration of a common hermetic encapsulation approach for implantable devices, such as 10, where non-bio-compatible components and materials 11, such as electronics, are encapsulated in a hermetically sealed package 12 made of bio-compatible materials. In this arrangement, an array of hermetic electrically conducting feedthroughs 13 is provided on an electrically insulating portion 14 of the package 12 for use as electrical conduits which allow communication of electrical signals between the body and electronics within the package.

Various methods are known to produce hermetic electrically conducting feedthroughs. However, they often tend to be high-cost, lack scalability, and have inherent material incompatibilities. For example, FIGS. 2A and 2B illustrate a method for producing metal feedthroughs in laser drilled holes on non-conductive substrates. In this method, a ceramic or other electrically non-conductive substrate 20 is laser drilled with holes 21. The holes are turned into feedthroughs by filling them with thick-film metal paste 22 which consists of metal particles in an organic solvent. The metal paste is typically pulled through the holes using vacuum and fired at high temperature to drive out the solvent, leaving only metal in the holes. This method however can be problematic because the thick-film metal paste can leave voids when fired or the adhesion of metal to substrate may be poor, either of which can cause leakage paths through the feedthroughs leading to heiinetic failure. Also the high-temperature firing can cause delamination of the metal from the ceramic due to the stresses induced from thermal expansion mismatch between the metal and the ceramic. And because hermetic package enclosures are typically made of bio-compatible metals which must be hermetically bonded to ceramic feedthrough substrates using a high temperature brazing process, this introduces an additional high temperature process which can further increase the chances of failure at the feedthrough-ceramic and also the ceramic-package interfaces. And the laser cutting process used to form holes introduces additional limitations. For example, laser cutting often causes micro-cracks in the ceramic substrate, making it fragile and limiting the minimum gap between adjacent holes. And the minimum diameter of the substrate holes is restricted due to tapering produced by the laser cutting process which limits feedthrough density. As illustrated in FIGS. 3A and 3B, there exists a trade-off between substrate thickness (scalability) and hermeticity. Shorter holes (in which shorter feedthroughs 26 are formed) in thinner ceramic substrate 25 of FIG. 3B, are easier to laser cut, but they are less likely to be hermetic since there is a smaller area for the metal to adhere to the ceramic. Thicker ceramic substrates, such as 23 in FIG. 3A, provide more surface area for the metal to adhere and improve hermeticity. However, they are harder to laser cut, and as can be seen by the four longer feedthroughs 24 in FIG. 3A in the same substrate area as six shorter feedthroughs 26 in FIG. 3B, feedthrough density is less than a thinner substrate due to hole taper.

Another known method of producing hermetic electrically conducting feedthroughs uses co-fired multi-layer ceramics, and illustrated in FIGS. 4A-4D. In this method, multiple layers of thin ceramics 30-33 are physically punched with holes 34-37, respectively. Each ceramic layer 30-33 is then metalized using thick-film metal paste, 38-41, respectively, to create the feedthroughs in the holes. As shown in FIG. 4D, the layers of ceramics 30-33 are then stacked and co-fired to create the final substrate with feedthroughs 43 extending through the stack. However, the size of holes formed using this method is often restricted to the dimension of the punching process (e.g. about 100-125 microns). And the mechanical fragility of substrates due to punching can restrict the pitch between adjacent holes.

In order to improve the longevity and effectiveness of implantable devices, it is advantageous to be able to fabricate durable hermetic electrically conductive feedthroughs which allow connection to hermetically sealed electronic devices. In particular, it would be advantageous to provide a scalable fabrication method for producing high-density, bio-compatible, hermetic electrically conductive feedthroughs in a range of substrate thicknesses, that improves the hermetic bond between feedthrough and insulator by using lower temperature process for insulator sealing.

SUMMARY

The technology described in this patent document includes devices, systems and methods for fabricating high-density hermetic electrical feedthroughs, and the feedthroughs produced thereby.

In one example implementation, a method of fabricating electrical feedthroughs is provided to include providing an electrically conductive substrate having opposing first and second sides; selectively removing substrate material from the first side of the substrate to four an array of electrically conductive posts in a substrate cavity; filling said substrate cavity with an electrically insulating material to surround each post therewith; solidifying the electrically insulating material; and exposing the solidified electrically insulating material from the second side of the substrate so that each post is electrically isolated as an electrical feedthrough extending between the first and second sides of the substrate.

In another example implementation, a method of fabricating electrical feedthroughs is provided to include providing an electrically conductive bio-compatible metal substrate having opposing first and second sides; selectively removing substrate material from the first side of the substrate to form an array of electrically conductive posts in a substrate cavity; filling said substrate cavity with an electrically insulating bio-compatible material to surround each post therewith; solidifying the electrically insulating material; and exposing the solidified electrically insulating material from the second side of the substrate so that each post is electrically isolated as an electrical feedthrough extending between the first and second sides of the substrate.

In another example implementation, a hermetic electrically conductive feedthrough construction is provided comprising an electrically conductive substrate having opposing first and second surfaces, a frame portion, and a post portion comprising an array of posts extending between the first and second surfaces, with each post electrically isolated from the frame portion and each other by an electrically insulating material solidified therebetween, as an array of electrically conductive feedthroughs.

These and other implementations and various features and operations are described in greater detail in the drawings, the description and the claims.

The present invention is generally directed to a method of fabricating low-resistance, high-density, hermetic, preferably bio-compatible, electrical feedthroughs from an electrically conductive substrate having opposing first and second sides, e.g. top and bottom surfaces. Electrical connections between the top and bottom surfaces can be made by creating electrically conductive feedthroughs (or vias) from the substrate material itself. As such, an electrically conductive substrate (e.g. metallic substrate) is provided to serve as both the bulk substrate and the feedthrough material. It is notable that various types of electrically conductive materials may be used for the electrically conductive substrate, especially materials having high electrical conductivity and stability in harsh environments. For bio-medical implant applications in particular, substrate materials that have high bio-compatibility and are capable of being hermetically sealed to implantable metal packages are preferred. Example bio-compatible electrically conductive substrate materials that may be used include: titanium and its alloys, such as surgical grade titanium—Ti6Al4V, Ti6Al4V ELI ('extra low interstitials') and niobium and alloys. While bio-compatible electrically conductive metal substrates are preferred in bio-medical implant applications, if the electrically conductive substrate material was further coated with an insulating material then any electrical conductor may be used, such as but not limited to platinum and alloys (such as platinum-iridium); iridium and alloys; ruthenium and alloys; Nitinol (Ti—Ni); palladium and alloys; rhodium and alloys, gold and alloys; copper and alloys; aluminum and alloys; surgical grade stainless steel such as 316LVM; p- or n-type doped silicon; etc. In any case, one of the advantages of using a metal substrate is the ability to anneal if micro-cracks appear from laser cutting.

Fabrication of the feedthroughs is generally accomplished by separating individual feedthroughs from electrically conductive bulk substrate material by patterning feedthrough posts on a first side (e.g. top surface) of the substrate. In particular, substrate material is first selectively removed from the first side of the substrate to form an array of electrically conductive posts each standing erect in a substrate cavity with one end fixed at the bottom of the cavity and an opposite free end adjacent the first side. The selective removal of substrate material does not penetrate the full depth of the substrate, and may be accomplished using various processes, such as for example, using a dicing saw, milling, laser machining, reactive ion etching, ion milling, mechanical dicing, electrical discharge machining, waterjet cutting, laser waterjet cutting, laser cutting, reactive-ion etching, deep reactive ion etching, ion-milling, etc. Increased feedthrough densities due to scalability of reactive ion etching; therefore scalable to thin or thick substrates. Using any of these methods, high and low aspect ratios of feedthroughs are possible without tapers typically seen in laser cutting processes which can severely limit the smallest pitch and diameters of the feedthrough holes that can be drilled. Using these post forming processes, post widths may range from about 10 μm to about 200 μm. And post height may range from about 50 μm to about 1000 μm. Density of posts/feedthroughs (center-to-center distance between posts) may range from about 50 μm to about 500 μm between posts. It is appreciated, however, that the array of electrically conductive posts includes a minimum of one post, with no maximum number of posts.

Once the array of posts are formed, the substrate cavity or cavities (i.e. the space surrounding the posts) is filled with an electrically insulating material (e.g. glass-, polymer-, ceramic-insulator) to surround each post. For example, the electrically insulating material may be a bio-compatible electrically insulating material, such as for example sealing glasses such as Pyrex, non-leaded glass, boro-silicate glass, glass-frit powder or paste, glasses or ceramics containing one or more of $B_2O_3$, CaO, BaO, $SiO_2$, $La_2O_3$, $Al_2O_3$, $Li_2O_3$, $TiO_2$, And the thermal expansion coefficient of the insulating material may be chosen to closely match that of the substrate to prevent thermal mismatch failures. In one embodiment, the electrically insulating material has a thermal expansion coefficient substantially matching that of the substrate (i.e. thermal expansion coefficient numbers are, for example, within 20% of both materials). The advantage of minimizing thermal expansion mismatch results in highly hermetic bonds between insulator and feedthrough. It is notable that the electrically insulating material is of a type cable of being flowed into the substrate cavity to fill said cavity. This promotes adhesion between the insulating material and the substrate and prevents voids.

After filling the substrate cavity (or cavities) the insulator material is solidified, such as by firing at elevated temperatures. Once fired and solidified, the electrically insulating material is exposed from the second side opposite the first side from which the substrate cavity was formed. In particular, the electrically insulating material is sufficiently exposed so that each post is electrically isolated as an electrical feedthrough extending between the first and second sides of the substrate. Exposure of the electrically insulating material from the second side (e.g. the bottom surface) may be achieved by mechanical lapping, polishing or otherwise grinding, such as conventionally known in the art. The first side (e.g. top surface) may also be lapped and polished. This produces a hermetic substrate with high-density electrical feedthroughs. It is notable that bio-compatible substrate or insulating material may be used in order to create a bio-compatible substrate or enclosure for implantation.

The present invention is also directed to a hermetic electrically conductive feedthrough construction and interface, having an electrically conductive substrate with opposing first and second surfaces. The electrically conductive substrate may also be characterized as having a frame portion, and a post portion separated from the frame portion. While both the frame and post portions are made of the same electrically conductive substrate material, the post portion is physically separated from the frame portion, with the frame portion generally surrounding and thereby supporting the post portion. The post portion in particular includes an array of posts extending between the first and second surfaces, with each post electrically isolated from the frame portion and each other by an electrically insulating material solidified therebetween. Insulated as such, the array of posts functions as an array of electrically conductive feedthroughs.

As previously discussed, hermetically sealed packages with electrical feedthroughs is commonly used by many companies in the bio-medical device industry to separate non-bio-compatible components from bodily tissue. However, electrical feedthroughs are also used in the semiconductor industry to interconnect electronic chips. And electrical feedthroughs may also be used in other applications, such as separating sensors or electronics from harsh environments in the field. It is appreciated therefore that while bio-compatible materials are preferred for use as one or both of the electrically conductive substrate/feedthroughs and electrically insulating materials of the present invention when used in bio-medical implant applications, other non-bio-compatible materials may be used in the alternative for other non-bio-medical applications. The challenge in all these applications, however, remains the same, that is to create very high-density hermetic feedthroughs using materials that are compatible with the environment of application.

DETAILED DESCRIPTION

Figure 5:
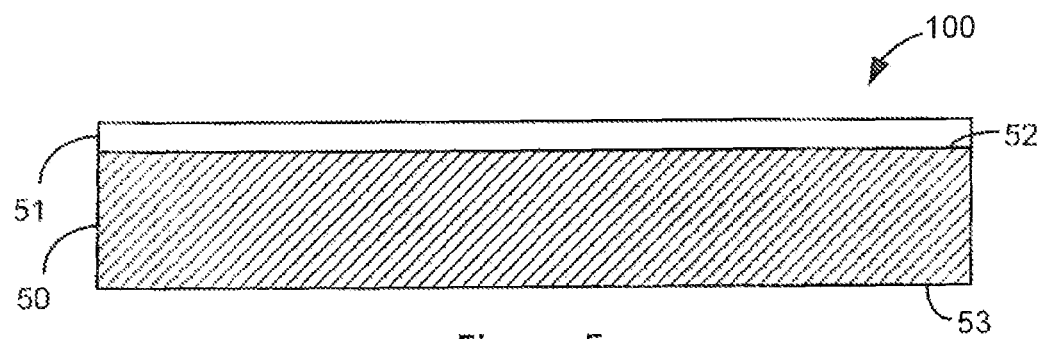
FIG. 5 is a cross-sectional view of a first stage of a first example method of the present invention employing an ion-milling process to remove substrate material to form an array of posts in a substrate cavity.
Figure 6:
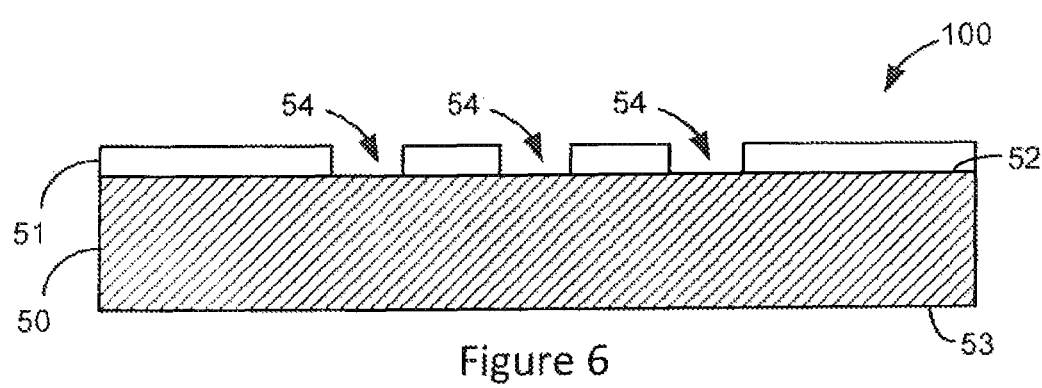
FIG. 6 is a cross-sectional view of a second stage following FIG. 5 of a first example method of the present invention employing an ion-milling process to remove substrate material to form an array of posts in a substrate cavity.
Figure 7:
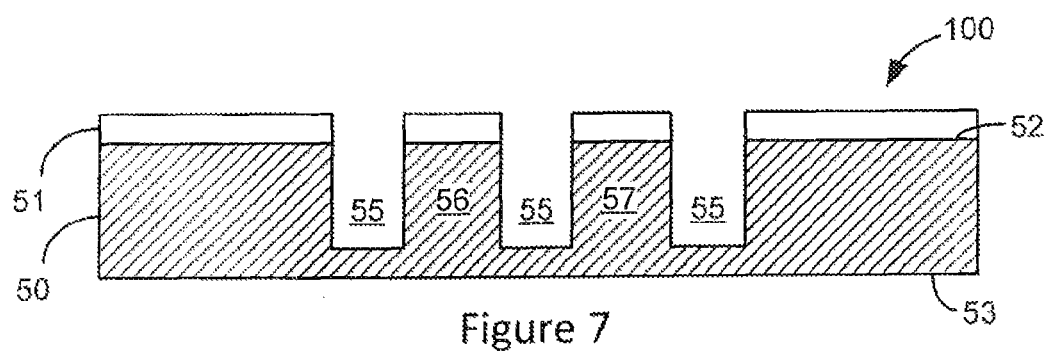
FIG. 7 is a cross-sectional view of a third stage following FIG. 6 of a first example method of the present invention employing an ion-milling process to remove substrate material to form an array of posts in a substrate cavity.

Turning now to the drawings, FIGS. 5-13 together illustrate a first example method of fabricating electrically conductive feedthroughs ("electrical feedthroughs"). In particular FIGS. 5-7 show the formation and use of an etch mask in an example ion-milling process for transferring an etch pattern used to selectively remove substrate material from an electrically conductive substrate, to form the substrate cavity and array of posts particularly shown in FIG. 8-13. It is appreciated, however, that the etch mask/ion-milling process shown in FIGS. 5-7 illustrate Only one example method of forming the substrate cavity and array of posts shown in FIG. 8. Other methods for selectively removing substrate material may be utilized as described in the Summary.

In FIG. 5, the beginnings of an exemplary feedthrough construction 100 is shown having an electrically conductive substrate 50 with opposing first 52 and second 53 sides (e.g. top and bottom surfaces, respectively), and an etch mask layer 51 formed on the first side 52. And FIG. 6 shows a desired etch pattern 54 formed on the mask layer 51 for selectively removing, via etching, substrate material to form the substrate cavity and the array of posts in the substrate cavity. Notably the etch pattern includes one or more isolated portions ("islands") of the etch mask layer which will define the individual posts to be formed. And the etch mask layer 51 is preferably of a type capable of supporting and withstanding an ion milling procedure for transferring the mask pattern of the etch mask to the underlying metal substrate as a substrate cavity or cavities. Various types of materials may be used for the etch mask layer, such as for example photoresist, high temperature polymer (i.e. capable of surviving temperatures greater than 120 degrees C., such as polyimide or parylene), or a metal of a different type than the underlying metal layer, as alternatives. With regard to a metal of a different type, the selectivity of the mask metal to the underlying metal substrate is important in order to be able to selectively strip the mask metal. For example, Al may be used as a etch mask for Pt and Au because Al etchant does not etch either Au or Pt or Ti or TiN etch.

While not shown in the figures, after forming the etch mask in FIG. 6, the substrate is placed in an ion mill, a reactive ion etcher, a deep reactive ion etcher, or other plasma system (hereinafter "ion mill") to selectively remove substrate material following the etch pattern. FIG. 7 shows the results of such ion milling process and the substrate cavity 55 and posts 56 and 57 thus formed. High temperature polymer etch masks may be selectively removed using $O_2$ plasma etch, and the metal hard etch mask may be removed using dry and/or wet etch techniques.

Figure 1:
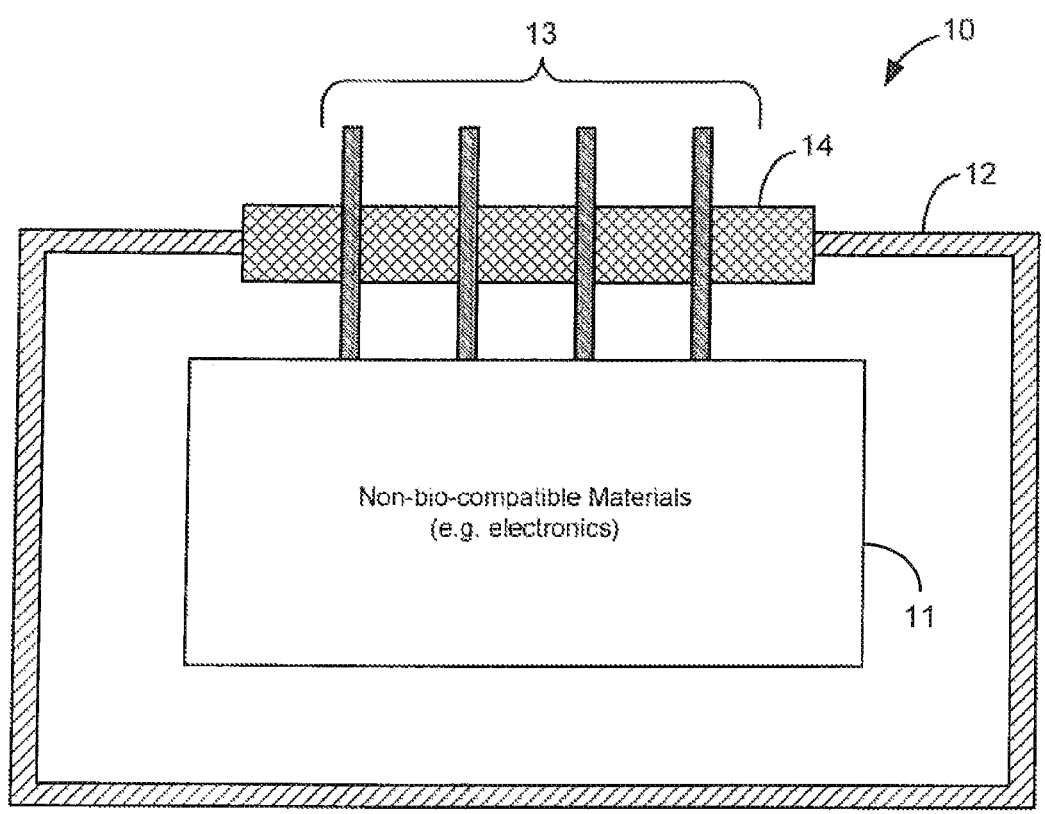
FIG. 1 is a schematic view of an implantable device illustrating a common approach to encapsulating non-bio-compatible component materials in a bio-compatible sealed package.
Figure 2A:
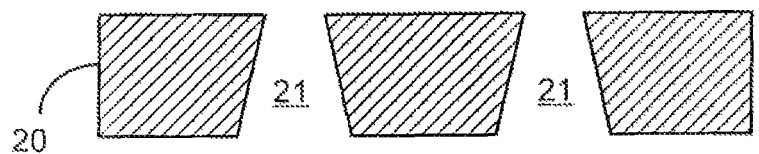
FIG. 2A is a cross-sectional view of a substrate with holes produced by laser cutting in a first example method of fabricating feedthroughs known in the art.
Figure 2B:
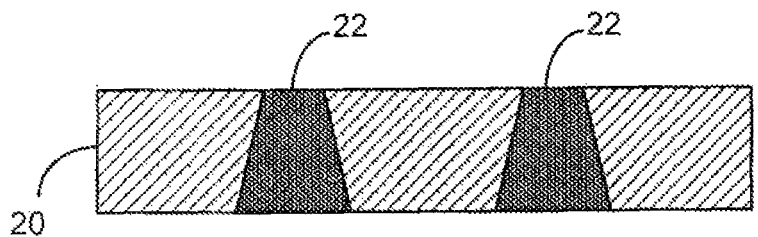
FIG. 2B is a cross-sectional view of the substrate in FIG. 2A after the laser-cut holes are filled with a metal from a metal paste.
Figure 3A:
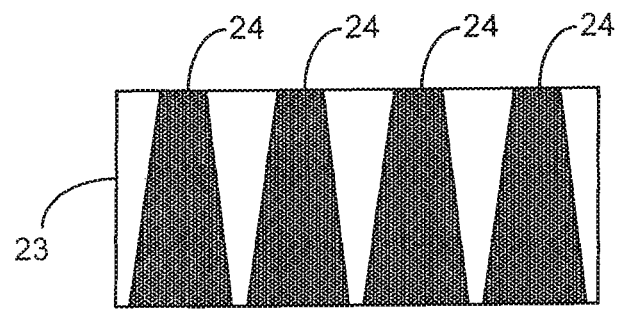
FIG. 3A is a cross-sectional view of an example thicker substrate produced by the method illustrated in FIGS. 2A-B illustrating, together with FIG. 3B the trade-off between substrate thickness (scalability) and hermeticity.
Figure 3B:
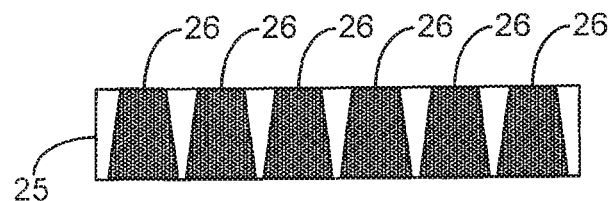
FIG. 3B is a cross-sectional view of an example thinner substrate produced by the method illustrated in FIGS. 2A-B illustrating, together with FIG. 3A the trade-off between substrate thickness (scalability) and hermeticity.
Figure 4A:
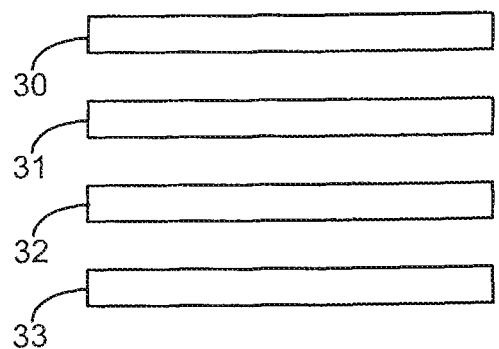
FIGS. 4A-D show four stages of a second example method of fabricating feedthroughs known in the art by co-firing multiple ceramic substrates.
Figure 4B:
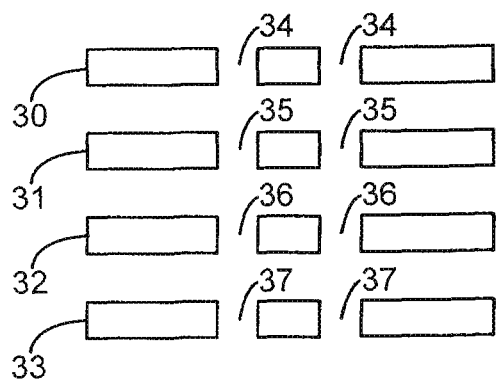
Figure 4C:
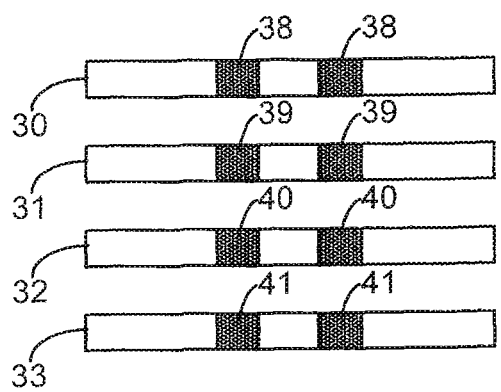
Figure 4D:
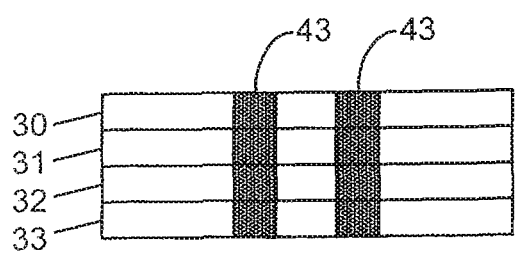
Figure 8:
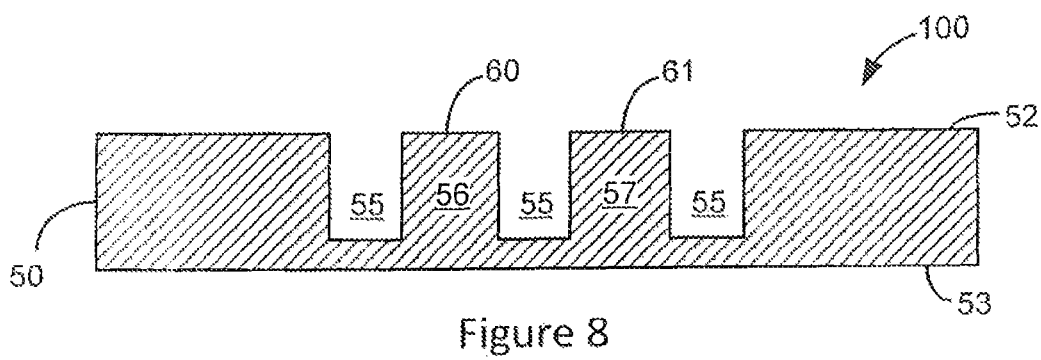
FIG. 8 is a cross-sectional view taken along line 8-8 of FIG. 9 of an exemplary substrate having posts in a substrate cavity formed by the removal of substrate material in an exemplary fabrication method of the present invention.
Figure 9:
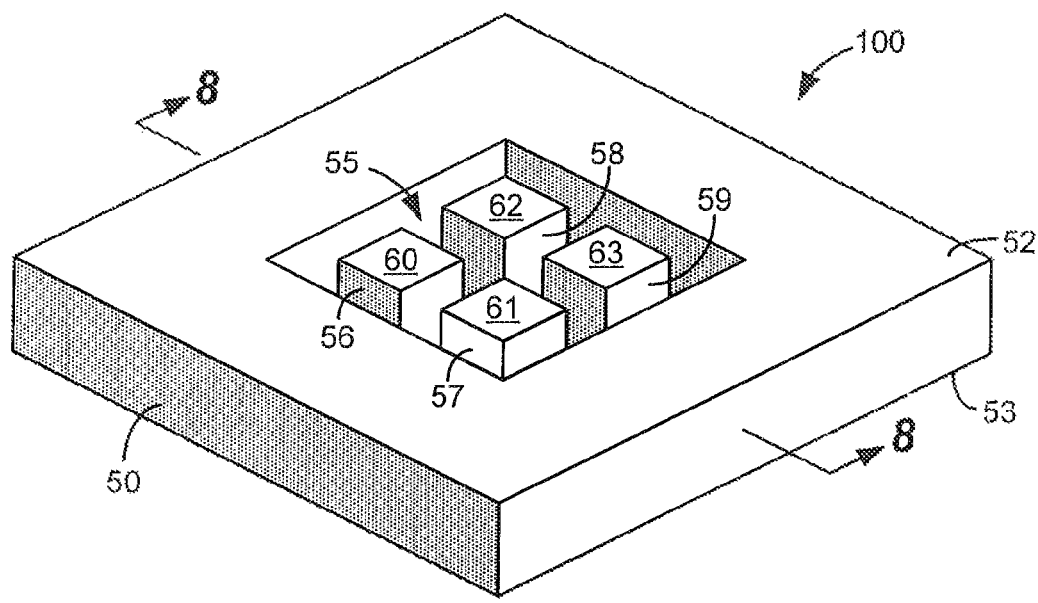
FIG. 9 is a perspective view of the exemplary substrate with posts of FIG. 8.
Figure 10:
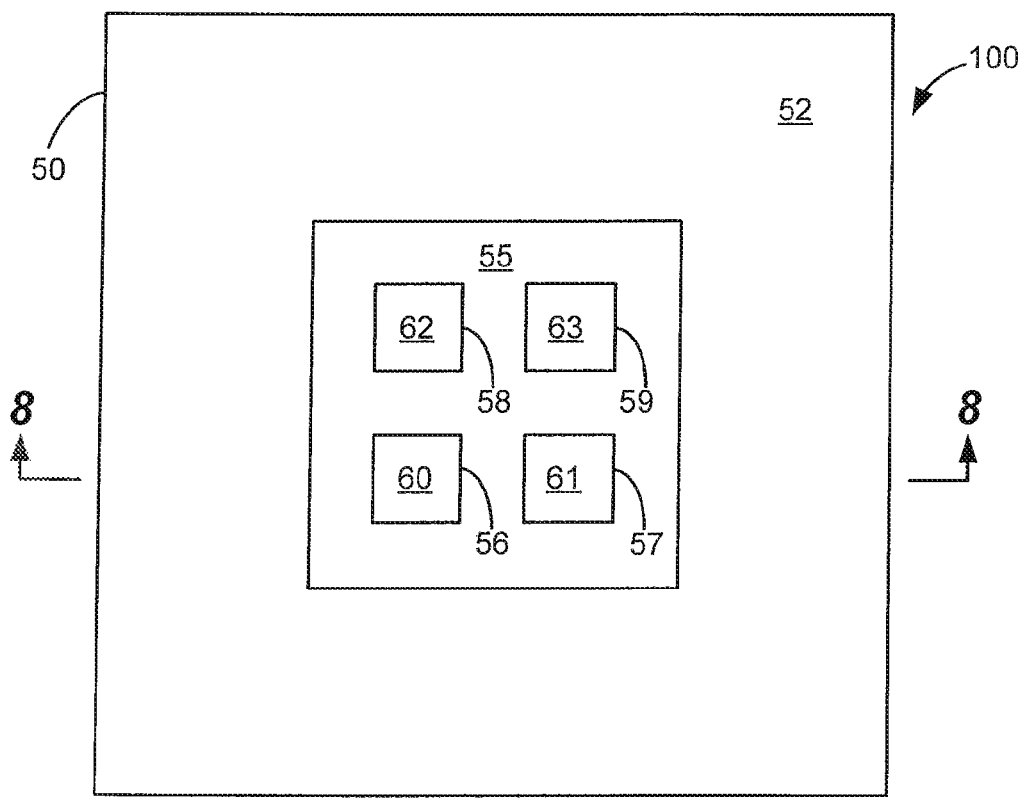
FIG. 10 is a top view of the exemplary substrate and posts of FIGS. 8 and 9.

FIG. 8 shows the posts 56 and 57 after selectively removing the remaining portions of the etch mask to expose the tops surfaces 60 and 61 of the posts 56 and 57. In particular, FIG. 8 is a cross-sectional view taken along line 8-8 of FIGS. 9 and 10 which show perspective and top views, respectively, of the feedthrough construction 100 and the four posts 56-59 formed in the substrate cavity 55. As shown in the figures, each of the posts 56-59 are generally erect structures having one end fixed in the cavity and an opposite free end adjacent the first side 52. While the posts are shown as rectangular blocks, it is appreciated that the post cross section is dependent on the etch pattern "islands" which is not limited to any particular shape. And while only four posts are shown, it is appreciated again that the array may include at least one post and no maximum number of posts. The array of posts 56-59 may be characterized together as a post portion of the electrically conductive substrate 50, while the bulk substrate surrounding the array of posts may be characterized as a frame portion of the electrically conductive substrate 50, since both are portions of and formed from the same substrate 50 albeit with different functionalities. The post portion is intended for use as the array of hermetic electrically conductive feedthroughs, and the frame portion intended as the support structure for connecting to the rest of a hermetically sealed package, such as 12 in FIG. 1.

Figure 11:
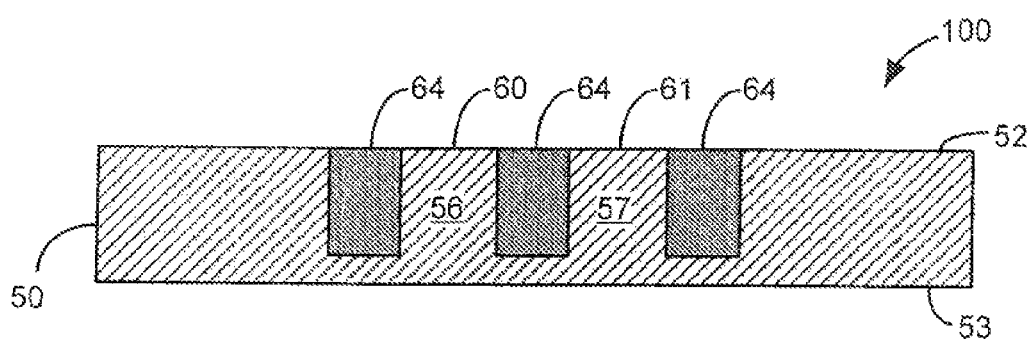
FIG. 11 is a cross-sectional view following FIG. 9 of the exemplary substrate after the substrate cavity is filled with an insulating material.

FIG. 11 shows a cross-sectional view of the feedthrough construction 100 following FIG. 8, in which the substrate cavity 55 is filled with an electrically insulating material 64 to surround each post, and subsequently solidified. For example, the cavity space around the posts may be filled with biocompatible sealing glasses and fired at elevated temperatures. The lower temperature process used for sealing glasses reduces thermal expansion mismatch. To prevent voids in the insulating material, and promote good adhesion, the electrically insulating material is flowed into the substrate cavity to surround each post. For example, there is reduced void formation because sealing glasses melt and fuse together. Solidification of the electrically insulating material may be achieved by heating at elevated temperatures (e.g. from about 300° C. to about 2000° C.).

Figure 12:
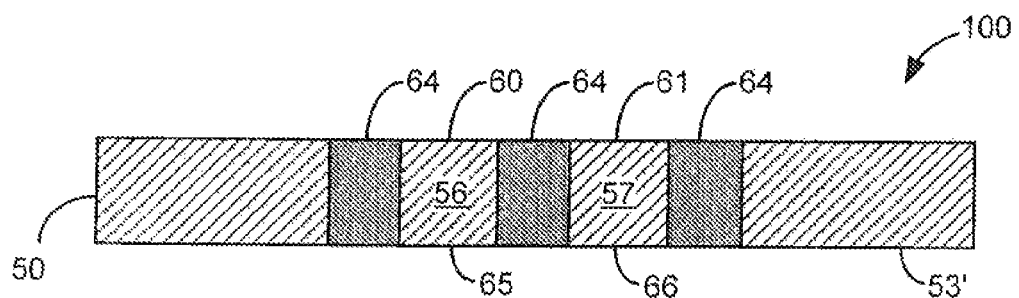
FIG. 12 is a cross-sectional view following FIG. 11 and taken along line 12-12 of FIG. 13 of the exemplary substrate after exposing the insulating material on an opposite side of the substrate from which the insulating material was filled, to electrically isolate the posts and thereby form the feedthroughs.
Figure 13:
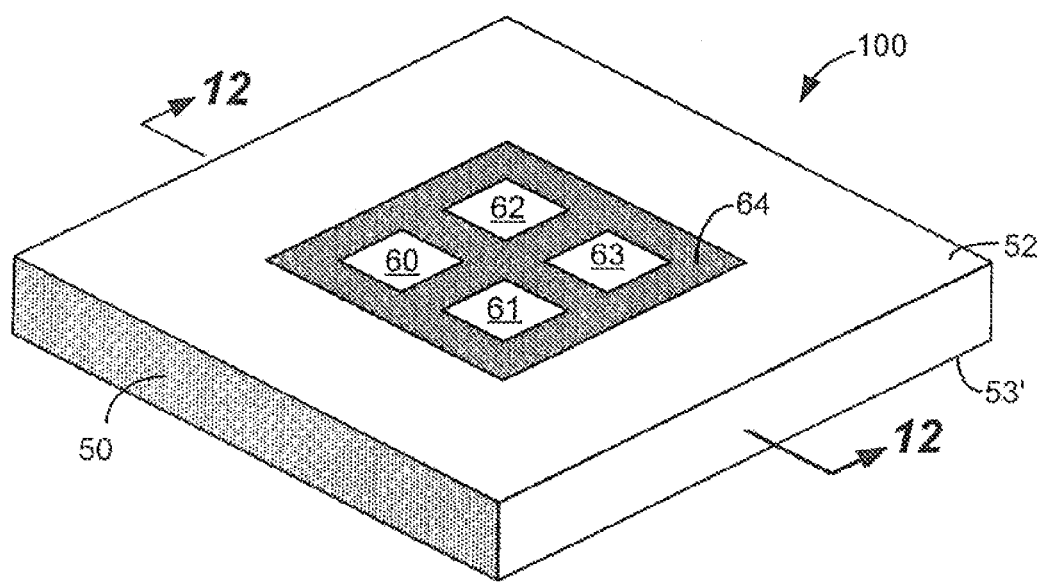
FIG. 13 is a perspective view of the electrically isolated feedthroughs of FIG. 12.

FIG. 12 shows a cross-sectional view of the feedthrough construction 100 following FIG. 11 and taken along line 12-12 of FIG. 13, after exposing the solidified electrically insulating material 64 from the second side 53 of the substrate 50 so that each post (e.g. 56, 57) is electrically isolated as an electrical feedthrough extending between the first and second sides of the substrate. In particular each post is electrically isolated from the bulk substrate (i.e. the frame portion) as well as all other posts. The exposing step may be performed by lapping, polishing or grinding the second side 53 until sufficient substrate material is removed for exposing the electrically insulating material. FIG. 12 shows how the exposing step has reduced the second side to a new surface 53' and new bottom post surfaces 65 and 66 of posts 56 and 57, respectively, opposite top post surfaces 60 and 61. And FIG. 13 shows the completed feedthrough structure 100 with four electrically isolated feedthroughs with only the top and bottom surfaces exposed on the first and second sides, respectively. In this manner, many such feedthroughs can be created on the same substrate to result in a high-density array of hermetic feedthroughs. Optionally, additional post-processing steps may include, for example, annealing the substrate and the array of electrically conductive posts, finely grinding and polishing the substrate flat on both sides, and metalizing and patterning for final application. Additionally, a second conformal coating (such as electroplating) to the back side may reduce via resistance.

Figure 14:
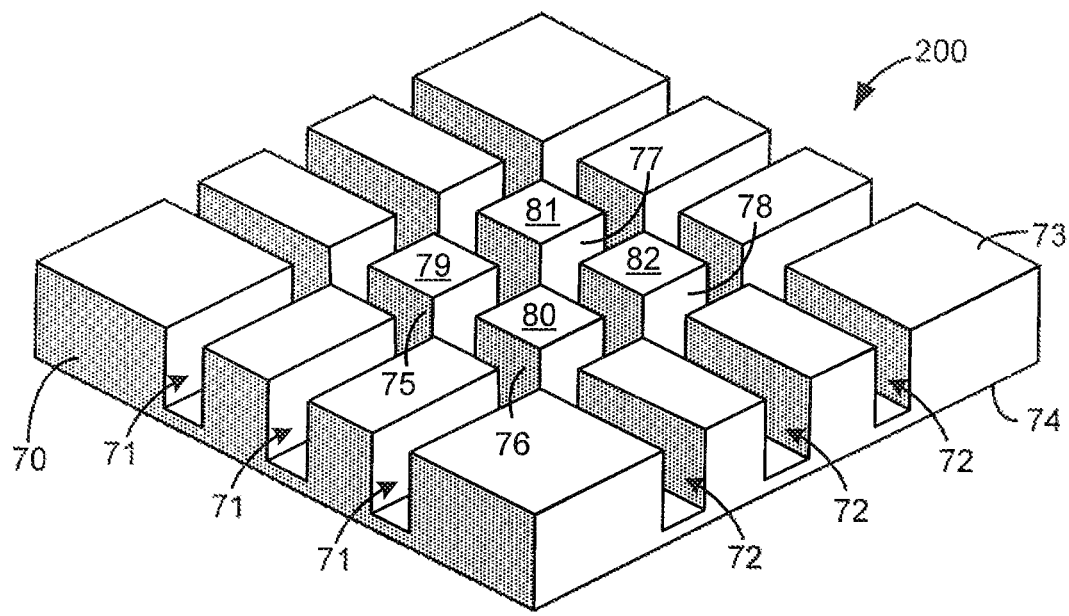
FIG. 14 is a perspective view of an exemplary substrate with posts in a substrate cavity formed by the removal of substrate material in another exemplary fabrication method of the present invention.
Figure 15:
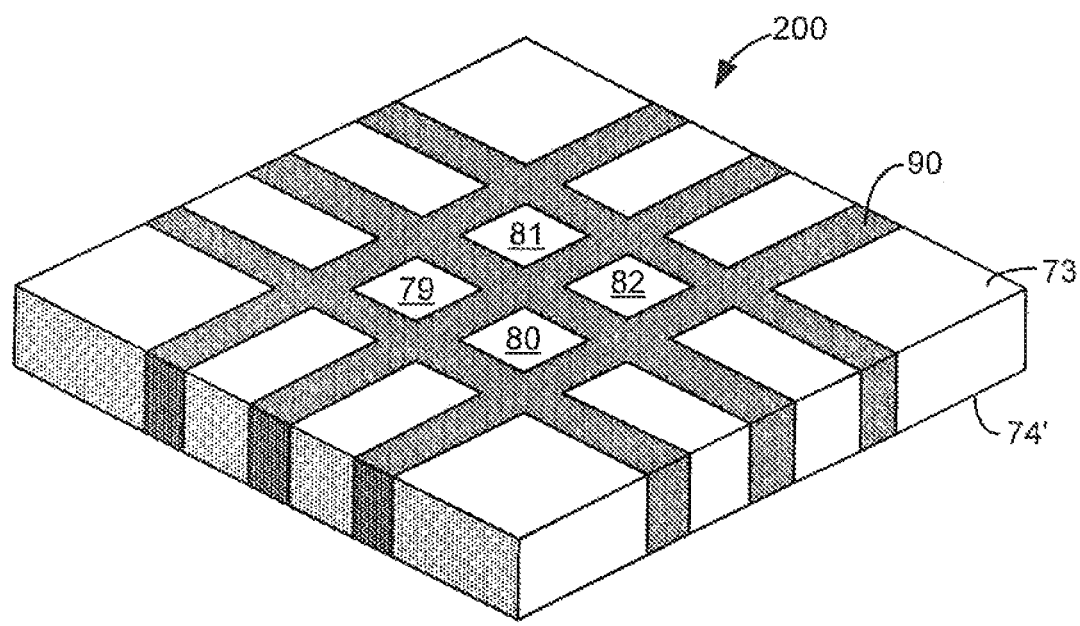
FIG. 15 is a perspective view following FIG. 14 of the electrically isolated feedthroughs formed after filling the substrate cavity with an insulating material and exposing the insulating material on an opposite side of the substrate from which the insulating material was filled.
Figure 16:
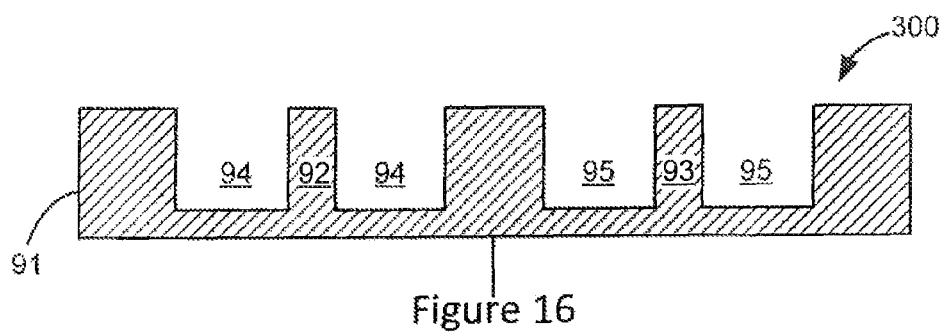
FIG. 16 is a cross-sectional view similar to FIG. 9 of an exemplary substrate having two cylindrical posts each in its respective cylindrical substrate cavity formed by the removal of substrate material in another exemplary fabrication method of the present invention.
Figure 17:
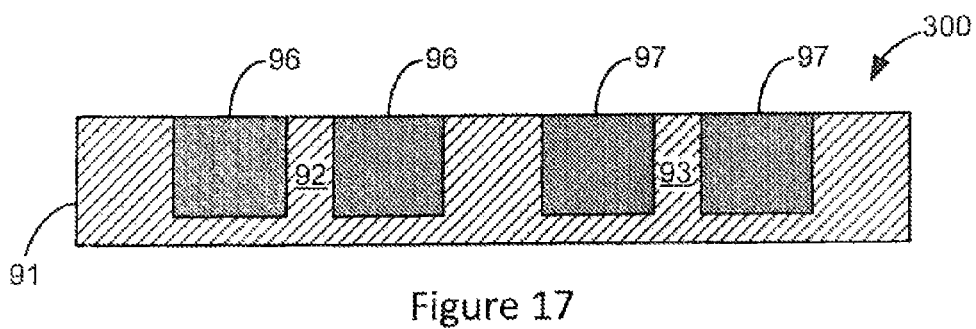
FIG. 17 is a cross-sectional view following FIG. 16 of the exemplary substrate after each of the substrate cavities is filled with an insulating material.
Figure 18:
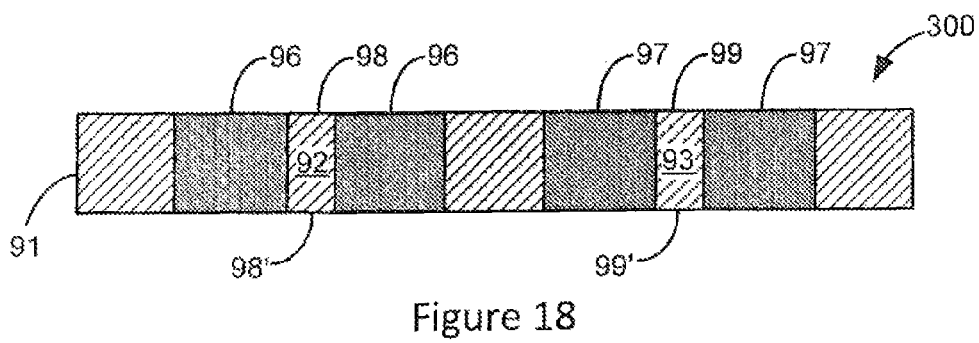
FIG. 18 is a cross-sectional view following FIG. 17 of the exemplary substrate after exposing the insulating materials on an opposite side of the substrate from which the insulating materials were filled, to electrically isolate the posts and thereby form the feedthroughs.
Figure 19:
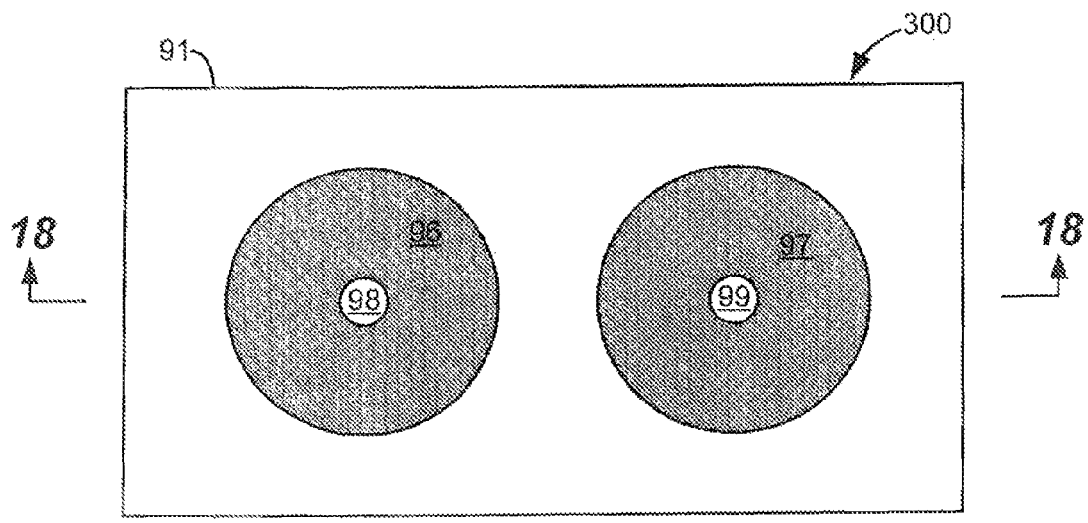
FIG. 19 is a top view of the exemplary substrate and two cylindrical feedthroughs of FIG. 18.

FIGS. 14 and 15 show another example embodiment of a feedthrough construction 200 formed from another example method of fabricating electrically conductive feedthroughs. In particular; the fabrication phase shown in FIG. 14 is analogous to FIGS. 8-10 after the substrate cavity and array of posts are formed but prior to filling with an electrically insulating material. Similar to FIGS. 8-10 the feedthrough construction 200 also has a first side 73 and an opposing second side 74 and four posts 75-82 formed in a substrate cavity fowled from the first side but does not extend through to the second side. The difference however, is that in FIG. 14, a sawing/milling process (e.g. using a dicing saw) is used to cut a first set of grooved channels 71 in one direction across the substrate, and a second set of grooved channels 72 in an orthogonal direction to the first set also across the substrate. The first and second sets of grooved channels together form the substrate cavity in which an electrically insulating material, such as 90 in FIG. 15, is used to fill. In particular, FIG. 15 shows the feedthrough construction 200 after exposing the solidified electrically insulating material 90 from the second side, shown as 74' so that each post (shown as top surfaces 79-82) is electrically isolated as an electrical feedthrough extending between the first and second sides of the substrate. It is notable that while FIG. 15 shows the insulating material 90 filling all of the grooved channels to the edges of the substrate 70, in the alternative, electrically insulating material need only be filled in a local area immediately surrounding the posts And FIGS. 16-19 show another exemplary embodiment of a feedthrough construction 300 formed from another example method of fabricating electrically conductive feedthroughs. In particular, FIG. 16 shows the selectively removal of substrate material from a substrate 91 such that two posts 92 and 93 are formed in independent substrate cavities 94 and 95, respectively. FIG. 17 show the filling and solidification of an electrically insulating material 96 and 97 in the cavities 94 and 95, respectively, and FIG. 18 shows the exposure of the electrically insulating materials from the second side opposite the first side from which the cavities were formed, so that post 92 has a top surface 98 and a bottom surface 98' exposed, and post 93 has a top surface 99 and a bottom surface 99' exposed. In this manner, each post 92 and 93 are electrically isolated from the bulk substrate (i.e. the frame portion); as well as each other. And FIG. 19 shows a top view of the exposed feedhrough construction of FIG. 18, illustrating the cylindrical geometry of both the posts/feedthroughs, as well as the substrate cavities.

Although the description above contains many details and specifics, these should not be construed as limiting the scope of the invention or of what may be claimed, but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

We claim:

1. A method of fabricating electrical feedthroughs, comprising:
   providing an electrically conductive substrate having opposing first and second sides;
   selectively removing substrate material from the first side of the substrate to form an array of electrically conductive posts in a substrate cavity;
   filling said substrate cavity with an electrically insulating material to surround each post therewith;
   solidifying the electrically insulating material; and
   exposing the solidified electrically insulating material from the second side of the substrate so that each post is electrically isolated as an electrical feedthrough extending between the first and second sides of the substrate.

2. The method of claim 1,
   wherein the electrically conductive substrate is a bio-compatible metal.

3. The method of claim 2,
   wherein the electrically conductive bio-compatible metal substrate is selected from the group consisting of titanium, platinum, iridium, ruthenium, niobium, palladium, gold, stainless steel, p- or n-type doped silicon, and alloys thereof.

4. The method of claim 1,
   wherein the electrically insulating material is a bio-compatible material.

5. The method of claim 4,
   wherein the electrically insulating bio-compatible material is selected from the group consisting of sealing glasses, non-leaded glass, boro-silicate glass, glass-frit powder or paste, and glasses or ceramics containing one or more of $B_2O_3$, $CaO$, $BaO$, $SiO_2$, $La_2O_3$, $Al_2O_3$, $Li_2O_3$, $TiO_2$.

6. The method of claim 1,
   wherein the electrically insulating material has a thermal expansion coefficient substantially matching that of the substrate.

7. The method of claim 1,
   wherein the substrate material is selectively removed by using a process selected from a group comprising using a dicing saw, milling, laser cutting, reactive ion etching, ion milling, mechanical dicing, electrical discharge machining, waterjet cutting, laser waterjet cutting, laser cutting, reactive-ion etching, deep reactive ion etching, and ion-milling.

8. A method of fabricating electrical feedthroughs, comprising:
   providing an electrically conductive bio-compatible metal substrate having opposing first and second sides;
   selectively removing substrate material from the first side of the substrate to form an array of electrically conductive posts in a substrate cavity;
   filling said substrate cavity with an electrically insulating bio-compatible material to surround each post therewith;
   solidifying the electrically insulating material; and
   exposing the solidified electrically insulating material from the second side of the substrate so that each post is electrically isolated as an electrical feedthrough extending between the first and second sides of the substrate.

9. The method of claim 8,
   wherein the electrically conductive bio-compatible metal substrate is selected from the group consisting of titanium, platinum, iridium, ruthenium, niobium, palladium, gold, stainless steel, p- or n-type doped silicon, and alloys thereof, and
   wherein the electrically insulating bio-compatible material is selected from the group consisting of sealing glasses, non-leaded glass, boro-silicate glass, glass-frit powder or paste, and glasses or ceramics containing one or more of $B_2O_3$, $CaO$, $BaO$, $SiO_2$, $La_2O_3$, $Al_2O_3$, $Li_2O_3$, $TiO_2$.

10. The method of claim 8,
    wherein the electrically insulating material has a thermal expansion coefficient substantially matching that of the substrate.

11. The method of claim 8,
wherein the substrate material is selectively removed by using a process selected from a group comprising using a dicing saw, milling, laser cutting, reactive ion etching, ion milling, mechanical dicing, electrical discharge machining, waterjet cutting, laser waterjet cutting, laser cutting, reactive-ion etching, deep reactive ion etching, and ion-milling.

12. A hermetic electrically conductive feedthrough construction, comprising:
an electrically conductive substrate having opposing first and second surfaces, a frame portion, and a post portion comprising an array of posts extending between the first and second surfaces, with each post electrically isolated from the frame portion and each other by an electrically insulating material solidified therebetween, as an array of electrically conductive feedthroughs.

13. The hermetic electrically conductive feedthrough construction of claim 12,
wherein the electrically conductive substrate is a bio-compatible metal.

14. The hermetic electrically conductive feedthrough construction of claim 13,
wherein the electrically conductive bio-compatible metal substrate is selected from the group consisting of titanium, platinum, iridium, ruthenium, niobium, palladium, gold, stainless steel, p- or n-type doped silicon, and alloys thereof.

15. The hermetic electrically conductive feedthrough construction of claim 12,
wherein the electrically insulating material is a bio-compatible material.

16. The hermetic electrically conductive feedthrough construction of claim 15,
wherein the electrically insulating bio-compatible material is selected from the group consisting of sealing glasses, non-leaded glass, boro-silicate glass, glass-frit powder or paste, and glasses or ceramics containing one or more of $B_2O_3$, CaO, BaO, $SiO_2$, $La_2O_3$, $Al_2O_3$, $Li_2O_3$, $TiO_2$.

17. The hermetic electrically conductive feedthrough construction of claim 12,
wherein the electrically insulating material has a thermal expansion coefficient substantially matching that of the substrate.

\* \* \* \* \*